United States Patent [19]

Regel et al.

[11] 4,239,765

[45] Dec. 16, 1980

[54] FLUORENYL-AZOLYLMETHYL-CARBINOL COMPOUNDS AND THEIR MEDICINAL USE

[75] Inventors: Erik Regel; Karl Büchel; Ingo Haller; Manfred Plempel, all of Wuppertal, Fed. Rep. of Germany

[73] Assignee: Bayer Aktiengesellschaft, Leverkusen, Fed. Rep. of Germany

[21] Appl. No.: 92,804

[22] Filed: Nov. 9, 1979

[30] Foreign Application Priority Data

Nov. 25, 1978 [DE] Fed. Rep. of Germany ....... 2851143

[51] Int. Cl.³ .................. C07D 233/60; A61K 31/415; A61K/31/41; C07D/249/12
[52] U.S. Cl. ............................... 424/269; 424/273 R; 548/262; 548/341

[58] Field of Search ....... 548/262, 341; 424/269, 273 R

[56] References Cited

U.S. PATENT DOCUMENTS

3,754,001  8/1973  Timmler et al. .................... 548/341

*Primary Examiner*—Henry R. Jiles
*Assistant Examiner*—Robert T. Bond

[57] ABSTRACT

The invention relates to fluorenylazolylmethylcarbinols and methods for their preparation. Also included are compositions containing said fluorenylazolylmethylcarbinols and methods for the use of said carbinols and compositions containing them as antimycotic agents.

14 Claims, No Drawings

FLUORENYL-AZOLYLMETHYL-CARBINOL COMPOUNDS AND THEIR MEDICINAL USE

The present invention relates to certain new fluorenylazolylmethyl-carbinol compounds to processes for their production and to their use as antimycotic agents.

It has already been disclosed that 9-azolyl-fluorene derivatives have a good antimycotic action (compare DE-OS (German Published Specification) 2,004,697 and DE-OS (German Published Specification) 2,053,080). However, their action is not always completely satisfactory, in particular their in vivo action against dermatophytes. According to the present invention we provide compounds which are fluorenyl-azolyl-methyl-carbinols of the general formula

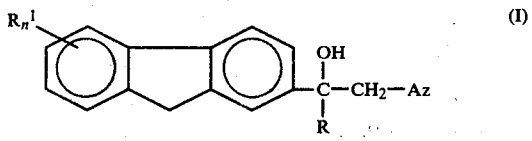

or a salt thereof in which

Az denotes an imidazole or triazole radical,

R denotes an optionally substituted phenyl, benzyl, naphthyl, naphthylmethyl, tetrahydronaphthyl or tetrahydronaphthylmethyl radical, $R^1$ denotes a halogen atom or an alkyl group and n is 0, 1 or 2.

The compounds of the present invention have powerful antimycotic properties.

According to the present invention there is further provided a process for the production of compounds of the present invention in which (a) a fluorenyl azolylmethyl ketone of the general formula

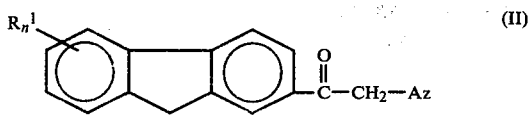

in which

Az, $R^1$ and n have the meanings indicated above, is reacted with a Grignard compound of the general formula $$R-Mg-X \quad (III)$$

in which

R has the meaning indicated above and

X denotes a halogen atom, preferably chlorine or bromine atom, in the presence of a diluent, or (b) a fluorenyl-halogenomethyl-carbinol of the general formula

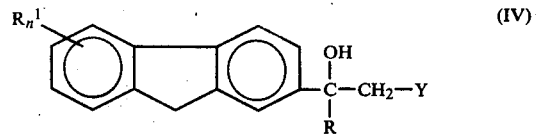

in which

R, $R^1$ and n have the meaning indicated above and

Y denotes a halogen atom, preferably a chlorine or bromine atom, is reacted with an azole of the general formula $$Z-Az \quad (V)$$

in which

Az has the meaning indicated above and

Z denotes a hydrogen atom or an alkali metal, preferably in the presence of acid-binding agent and preferably in the presence of a diluent.

The fluorenyl-azolyl-methyl-carbinols of the formula (I) obtainable according to the invention can furthermore be converted into salts by reaction with acids. Among the new fluorenyl-azolyl-methyl-carbinol salts of the invention, those salts that are pharmaceutically acceptable are particularly important and are preferred.

Surprisingly, the fluorenyl-azolyl-methyl-carbinols according to the invention display a better, therapeutically usable activity, in particular against dermatophytes, than known 9-azolyl-fluorene derivatives which are closely related compounds chemically and from the point of view of their action. The active compounds according to the invention thus represent a valuable advance in pharmacy.

Preferred fluorenyl-azolyl-methyl-carbinols of the formula (I) according to the invention are those in which Az denotes an imidazol-1-yl, 1,2,4-triazol-1-yl or 1,3,4-triazol-1-yl radical; R denotes an optionally (preferably mono- or di-) substituted phenyl, benzyl, naphthyl, naphthylmethyl, tetrahydronaphthyl or tetrahydronaphthylmethyl radical, preferred substituents being; halogen, in particular fluorine, chlorine and bromine, straight-chain or branched alkyl and alkoxy with in each case 1 to 4 carbon atoms, and halogeno-alkyl with 1 to 4 carbon atoms and up to 5 halogen atoms, in particular with 1 or 2 carbon atoms and up to 3 identical or different halogen atoms, halogens being, in particular, fluorine and chlorine, and trifluoromethyl being mentioned as an example: $R^1$ denotes a fluorine, chlorine or bromine aton or an alkyl group with 1 to 4 carbon atoms, and n is 0, 1 or 2.

Very particularly preferred compounds of the formula (I) are those in which Az denotes an imidazol-1-yl or 1,2,4-triazol-1-yl radical; R denotes a phenyl or benzyl radical, which is optionally monosubstituted or disubstituted by chlorine, fluorine or methyl, or denotes a naphthyl, naphthylmethyl, tetrahydronaphthyl or tetrahydronaphthylmethyl radical; $R^1$ denotes a chlorine or fluorine atom or a methyl, ethyl or isopropyl group and n is 0 or 1.

The following compounds of the general formula (I) may be mentioned specifically, in addition to the compounds mentioned in the preparation examples:

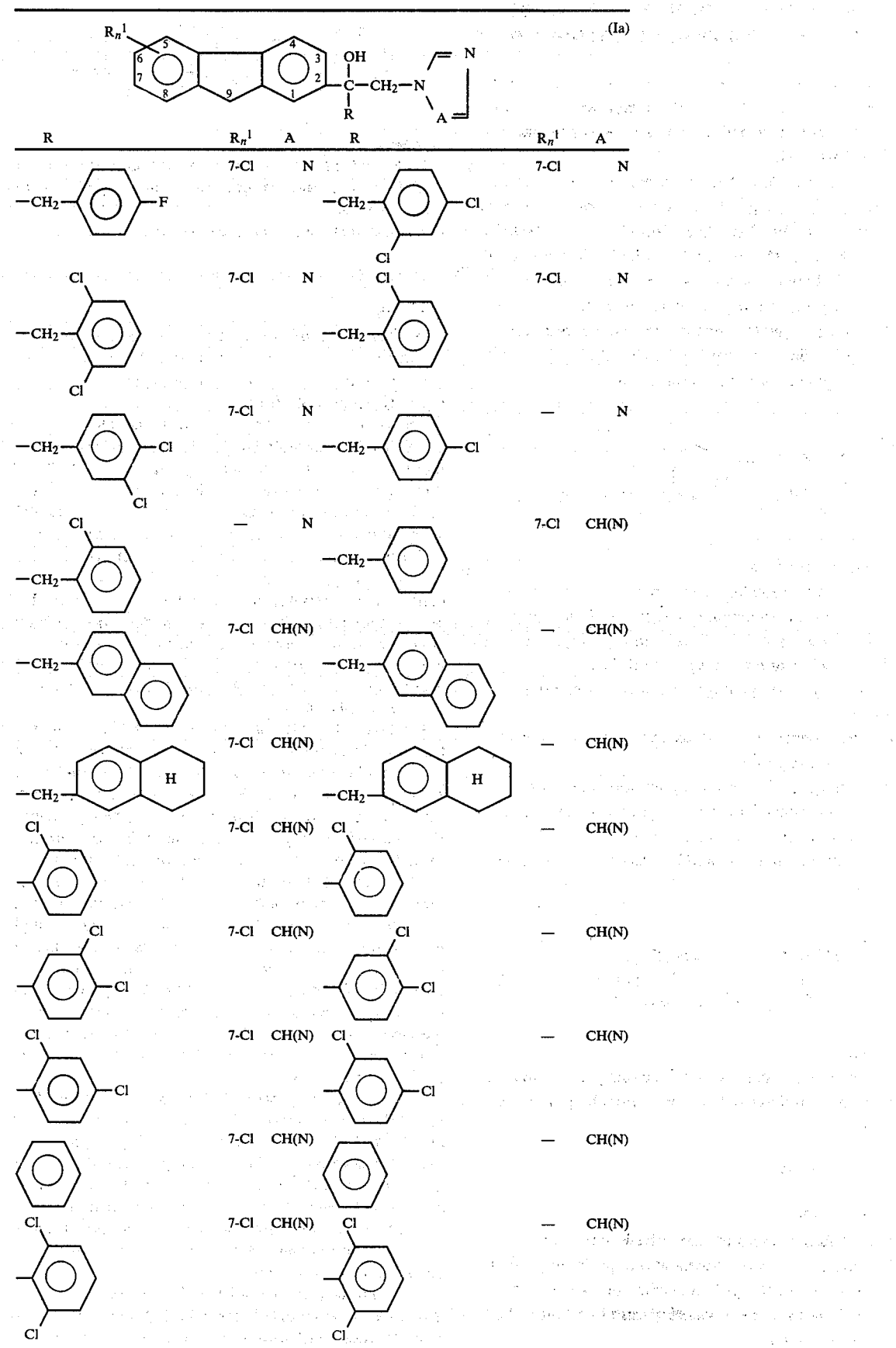

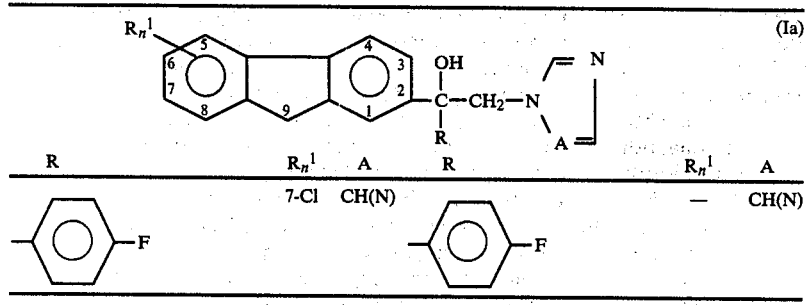

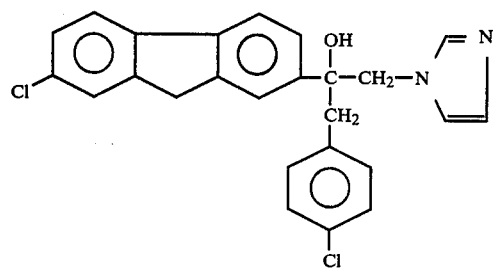

If, for example, fluoren-2-yl imidazol-1-yl-methyl ketone and 4-chlorophenyl-magnesium chloride are used as starting materials, the course of the reaction can be represented by the following equation (process variant (a)):

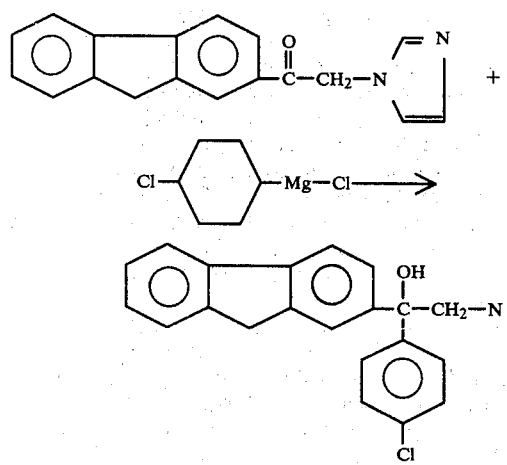

If, for example, 1-chloro-2-(7-chlorofluoren-2-yl)-3-(4-chlorophenyl)-propan-2-ol and sodium imidazole are used as starting materials, the course of the reaction can be represented by the following equation (process variant (b));

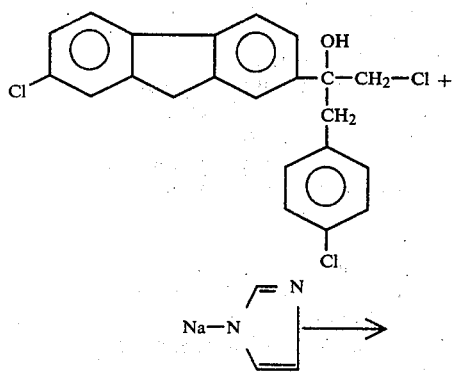

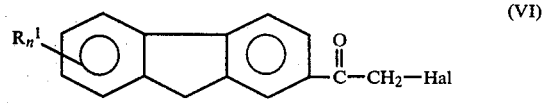

In the formula (II) Az and $R^1_n$ preferably represent those radicals which have already been mentioned in the case of the preferred and very particularly preferred compounds of the formula (I).

The fluorenyl azolymethyl ketones of the formula (II) are not yet known. However, they can be prepared in known manner, by reacting corresponding fluoreneacyl halides of the general formula (VI)

in which $R^1$ and n have the meaning indicated above and

Hal denotes a chlorine or bromine atom, with azoles in the presence of a diluent, such as, for example, dimethylformamide, and in the presence of an acid-binding agent, such as, in particular, an excess for azole, at temperatures between 20° and 80° C. (in this context, compare also the statements in U.S. Pat. No. 3,658,813).

Examples of the starting materials of the formula (II) are: fluoren-2-yl imidazol-1-yl-methyl ketone, 7-chlorofluoren-2-yl imidazol-1-yl-methyl ketone, 7-fluorofluoren-2-yl imidazol-1-yl-methyl ketone, 6-chlorofluoren-2-yl imidazol-1-yl-methyl ketone, 5-chlorofluoren-2-yl imidazol-1-yl-methyl ketone, 7-methylfluoren-2-yl imidazol-1-yl-methyl ketone, 7-ethylfluoren-2-yl imidazol-1-yl-methyl ketone, 7-isopropylfluoren-2-yl imidazol-1-yl-methyl ketone, 6-methylfluoren-2-yl imidazol-1-yl-methyl ketone and 5-methylfluoren-2-yl imidazol-1-yl-methyl ketone, and the corresponding 1,2,4-triazol-1-yl ketones and 1,34-triazol-1-yl ketones.

In the formula (III) R preferably represents those radicals which have already been mentioned in the case of the preferred and very particularly preferred compounds of the formula (I).

The Grignard compounds of the formula (III) are generally known compounds of organic chemistry. Examples which may be mentioned are: phenyl-magnesium chloride, 4-chlorophenyl-magnesium chloride, 2,4-dichlorophenyl-magnesium chloride, 2,6-dichlorophenyl-magnesium chloride, 2-chloro-6-fluorophenyl-magnesium chloride, 2-chlorophenyl-magnesium chloride, 3-chlorophenyl-magnesium chloride, 3,4-dichlorophenyl-magnesium chloride, naphth-2-yl-magnesium chloride, 1,2,3,4-tetrahydronaphth-6-yl-magnesium chloride, benzyl-magnesium chloride, 4-chlorobenzyl-magnesium chloride, 2,4-dichlorobenzyl-magnesium chloride, 2,6-dichlorobenzyl-magnesium chloride, 2-chloro-6-fluorobenzyl-magnesium chloride, 2-chlorobenzyl-magnesium chloride, 3-chlorobenzyl-magnesium chloride, 3,4-dichlorobenzyl-magnesium chloride, naphth-2-yl-methyl-magnesium chloride and 1,2,3,4-tetrahydro-naphth-6-yl-methyl-magnesium chloride, and the corresponding bromides.

In the formula (IV) R and $R^1_n$ preferably represent those radicals which have already been mentioned in the case of the preferred and very particularly preferred compounds of the formula (I).

The fluorenyl-halogenomethyl-carbinols of the formula (IV) are not yet known. However, they can be prepared in a generally customary and known manner by reacting ketones of the formula (VI) with Grignard compounds of the formula (III) according to process variant (a) (in this context, compare also the statements in DE-OS (German Published Specification) 2,623,129 and the preparation examples, corresponding to British Patent 1,532,156).

In the formula (V) Az preferably represents those radicals which have already been mentioned in the case of the preferred and very particularly preferred compounds of the formula (I), and Z preferably denotes hydrogen, sodium or potassium. The azoles of the formula (V) are generally known compounds of organic chemistry.

Possible diluents for the reaction, according to the invention, in process (a) are all the solvents customary for a Grignard reaction. These include, preferably, ethers, such as diethyl ether or tetrahydrofurane as well as mixtures with other organic solvents, such as, for example benzene.

The reaction temperatures can be varied within a substantial range in process (a). Preferably the reaction is carried out between 20° and 120° C., more preferably between 30° and 80° C.

In carrying out process (a), an excess of 3 to 5 mols of the Grignard compound of the formula (III) are preferably employed per 1 mol of the compound of the formula (II). Isolation of the compounds of the formula (I) is effected in a customary and known manner.

Preferred possible diluents for the reaction, according to the invention, in process (b) are inert organic solvents. These include, preferably, ketones, such as diethyl ketone, and in particular acetone and methyl ethyl ketone; nitriles such as propionitrile, and in particular acetonitrile; alcohols, such as ethanol or isopropanol; ethers, such as tetrahydrofurane or dioxane; aromatic hydrocarbons, such as benzene, toluene or dichlorobenzene; formamides, such as, in particular dimethylformamide; and halogenated hydrocarbons, such as methylene chloride, carbon tetrachloride or chloroform.

If process (b) according to the invention is carried out in the presence of an acid-binding agent, it is possible to add all the inorganic or organic acid-binding agents which can customarily be used, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylmethylamine and N,N-dimethylbenzylamine, and furthermore pyridine and diazabicyclooctane. The said alkylamines preferably contain 1 to 6 carbon atoms, the said cycloalkylamines preferably are those having 4 to 7 ring members and said aralkyl amines are preferably benzenoid in the aromatic portion and contain 1 to 2 carbon atoms in the alkyl portion. An excess of azole is preferably used.

The reaction temperatures can be varied within a substantial range in process (b). Preferably the reaction is carried out between 30° and 200° C., more preferably at the boiling point of the solvent.

In carrying out process (b) according to the invention, 1 to 2.5 mols of azole and 1 to 2.5 mols of acid-binding agents are preferably employed per 1 mol of the compounds of the formula (IV). If an alkali metal salt is used, 1 to 51.5 mols of alkali metal salt are preferably employed per 1 mol of the compound of the formula (IV). In order to isolate the compounds of the formula (I), the solvent is distilled off and the residue is washed with water directly or after being taken up in an organic solvent, and the organic phase is appropriately dried over sodium sulphate and freed from solvent in vacuo. If appropriate, the residue is purified by distillation, recrystallisation or chromatography.

All the acids which give rise to physiologically acceptable salts can be used for such salt preparation. These acids include, preferably, the hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid, pamoic acid and lactic acid, and sulphonic acids and 1,5-naphthalenedisulphonic acid.

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The compounds of the present invention, display antimicrobial actions, in particular antimycotic actions. They possess a very broad antimycotic action spectrum, especially against dermatophytes and blastomyces as well as biphase fungi, for example against varieties of Candida, such as *Candida albicans*, varieties of Epidermophyton, such as *Epidermophyton floccosum*, varieties as Aspergillus, such as *Aspergillus niger* and *Aspergillus fumigatus*, varieties of Trichophyton, such as *Trichophyton mentagrophytes*, varieties of Microsporon, such as *Microsporon felinuem* and varieties of Penicillium, such as *Penicillium commune*. This listing of micro-organisms in no way implies a limitation of the germs which can be combated but is only illustrative.

Examples which may be mentioned of fields of application in medicine are: dermatomycoses and systemic mycoses caused by *Trichophyton mentagrophytes* and other varieties Trichophyton, varieties of Microsporon, *Epidermophyton floccosum*, blastomyces and biphase fungi as well as moulds.

The present invention provides a pharmaceutical composition containing as active ingredient a compound of the invention in admixture with a solid or liquefied gaseous diluent, or in admixture with a liquefied diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets, (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsuled and pills include the following:

(a) fillers and extenders, e.g. starch, sugars, mannitol, and silicic acid; (b) binding agents; e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrysalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 2.5 g to 10 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably parenterally, especially intravenously. Preferred pharmaceutical compositions and medicaments are therefore those adapted for administration such as parenteral administration. Administration in the method of the invention is preferably parenteral administration.

In general it has proved advantageous to administer orally amounts of from 10 mg to 300 mg/kg, preferably 50 mg to 200 mg/kg, of body weight per day, optionally in the form of several individual administrations, to achieve effective results. Nevertheless, it can at times be necessary to deviate from those dosage rates, and in particular to do so as a function of the nature and body weight of the warm-blooded animal subject to be treated, the indivisual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day. Similar dosage rates are contemplated.

The following Examples A to C illustrate the in vitro and in vivo activity of compounds of the present invention.

EXAMPLE A

Antimycotic in vitro activity

Description of the experiment

The in vitro tests were carried out in a series dilution test with germ inocula of an average of $5 \times 10^4$ germs/ml of substrate. The nutrient medium was (a) for dermatophytes and moulds: Sabouraud's milieu d'épreuve and (b) for yeasts: means extract/glucose broth.

The incubation temperature was 27° C. and the duration of incubation was 24 to 96 hours.

In these tests, the active compounds according to the invention exhibited very good minimum inhibitory concentration values and thus proved superior to the known compounds.

EXAMPLE B

Antimicrobial in vivo activity (oral) in candidosis of mice

Description of the experiment

Mice of the SPF-CF type were infected intravenously with $1-2 \times 10^6$ logarithmically growing Candida cells, which were suspended in physiological sodium chloride solution. The animals are treated orally one hour before and seven hours after the infection, with, in each case, 50–100 mg/kg of body weight of the formulations.

Results

Untreated animals died 3 to 6 days after infection. The survival rate on the 6th day after infection was about 5% in the case of untreated control animals.

The known comparison compounds exhibited no action. In contrast, the compound, according to the invention, of Example 2 exhibited a very good action (>90% of survivors on the 6th day after infection).

EXAMPLE C

Antimycotic in vivo activity (oral) using experimental trichophytosis of guinea pigs as an example Description of the experiment White guinea pigs of the Pirbright white race were infected on their shaved, non-scarified backs with a microconidia and macroconidia suspension of Trichophyton mentagrophytes. The typical pattern of dermatophytosis with reddening, scaling and loss of hair up to total integumentary defect at the point of infection developed on untreated animals within 12 days after infection. The infected animals were treated locally once daily, starting on the 3rd day after infection, with 1% strength solutions of the preparations according to the invention in polyethylene glycol.

On the 14th day after infection, the untreated control animals and the animals treated with the comparison active compounds exhibited the typical pattern of dermatophytosis, whilst the test preparations had inhibited the progress of the infection.

In these tests, the compounds according to the invention exhibit very good local in vivo activities and thus proved superior to the known compounds.

The following Examples illustrate the preparation of compounds of the present invention.

EXAMPLE 1

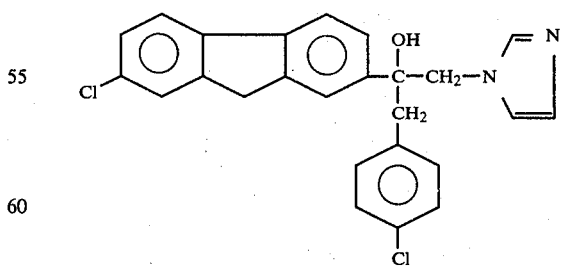

(Process b)

9 g (0.12 mol) of imidazole are added to a solution of 4.2 g (0.078 mols) of sodium methylate in 22 ml of methanol; a solution of 2-(7-chlorofluoren-2-yl)-3-chloro-1-(4-chlorophenyl)-propan-2-ol in 45 ml of dimethylformamide is then added dropwise and the mixture is warmed to 60° C. for 90 minutes. The mixture is poured into 2,000 ml of water, the crystalline mass which has separated out is dissolved in methylene chloride, the solution is washed with water, dried over sodium sulphate and filtered and the filtrate is concentrated in vacuo. The residue is made to crystallise by stirring with diethyl ether; the crystals are stirred with a little methyl alcohol and filtered off. 16.2 g (62.5% of theory) of 2-(7-chlorofluoren-2-yl)-1-(4-chlorophenyl)-3-(imidazol-1-yl)-propan-2-ol of melting point 218° C. are obtained.

Preparation of the starting material

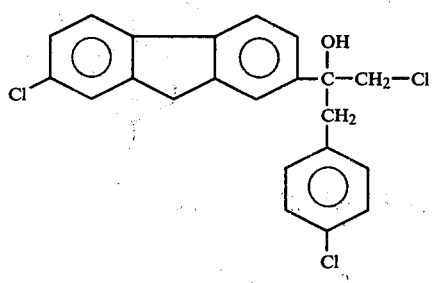

27.7 g (0.1 mol) of 2-(7-chlorofluoren-2-yl) chloromethyl ketone are added in portions to a solution of 4-chlorobenzyl-magnesium chloride obtained from 5.4 g (0.22 mol) of magnesium and 32.2 g (0.2 mol) of 4-chlorobenzyl chloride in 90 ml of diethyl ether, and the mixture is subsequently stirred for 1 hour. The mixture is poured onto ammonium chloride solution and the ether phase is seperated off, washed with water and dried over sodium sulphate. The oil obtained is made to crystallise by stirring with diisopropyl ether. 24.3 g (61% of theory) of 2-(7-chlorofluoren-2-yl)-3-chloro-1-(4-chlorophenyl)-propan-2-ol of melting point 108° C. are obtained.

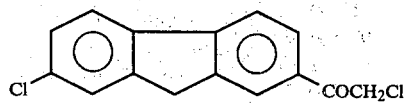

293.7 g (2.2 mols) of aluminium chloride are introduced in portions into a solution of 401 g (2.0 mols) of 2-chlorofluorene and 176 ml (2.2 mols) of chloroacetyl chloride in 1,000 ml of methylene chloride at 0° C. After 1 hour, ice-cold dilute hydrochloric acid is added to the mixture and the organic phase is washed with water, dried over sodium sulphate and concentrated in vacuo. The crystals obtained are stirred with ethyl alcohol and filtered off. 426.3 g (77% of theory) of 2-(7-chlorofluoren-2-yl) chloromethyl ketone of melting point 180° C. are obtained.

The compounds of Table 1 which follows are obtained in a corresponding manner.

TABLE 1

| Example No. | R | $R_n^1$ | Az | Melting Point (°C.) |
|---|---|---|---|---|
| 2 | —CH$_2$—C$_6$H$_4$—F | 7-Cl | Imidazol-1-yl | 210 |
| 3 | —CH$_2$—C$_6$H$_3$(Cl)—Cl | 7-Cl | Imidazol-1-yl | 222 |
| 4 | —CH$_2$—C$_6$H$_4$(Cl) | 7-Cl | Imidazol-1-yl | 214 |
| 5 | —CH$_2$—C$_6$H$_3$(Cl)(Cl) | 7-Cl | Imidazol-1-yl | 140 |
| 6 | —CH$_2$—C$_6$H$_3$(Cl)—Cl | 7-Cl | Imidazol-1-yl | 135 |
| 7 | —CH$_2$—C$_6$H$_4$—Cl | — | Imidazol-1-yl | 196 |
| 8 | —CH$_2$—C$_6$H$_4$(Cl) | — | imidazol-1-yl | 156 |
| 9 | —C$_6$H$_4$—Cl | 7-Cl | Imidazol-1-yl | 242 |
| 10 | —C$_6$H$_4$—Cl | — | Imidazol-1-yl | 238 |
| 11 | —CH$_2$—C$_6$H$_5$ | 7-Cl | Imidazol-1-yl | 255 |
| 12 | —C$_6$H$_4$—Cl | 7-Cl | 1,2,4-Triazol-1-yl | 186 |
| 13 | —C$_6$H$_4$—Cl | — | 1,2,4-Triazol-1-yl | |
| 14 | —CH$_2$—C$_6$H$_4$—Cl | 7-Cl | 1,2,4-Triazol-1-yl | |
| 15 | —C$_6$H$_4$—CL | 7-Cl | 1,3,4-Triazol-1-yl | 214 |

The present invention also comprises pharmaceutically acceptable biprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is coverted in the animal's body to the active compound.

What is claimed is:

1. A fluorenyl-azolylmethyl-carbinol of the formula

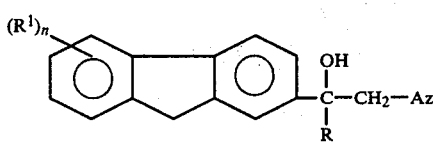

or a physiologically acceptable acid addition salt thereof in which Az denotes an imidazol-1-yl, 1,2,4-triazol-1-yl or 1,3,4-triazol-1-yl radical, R denotes a phenyl, benzyl, naphthyl, naphthylmethyl, tetrahydronaphthyl or tetrahydronaphthylmethyl radical optionally substituted by halogen, straight-chain or branched alkyl or alkoxy with in each case 1 to 4 carbon atoms, or halogenoalkyl with 1 to 4 carbon atoms and up to 5 halogen atoms, $R^1$ denotes a fluorine, chlorine or bromine atom or an alkyl group with 1 to 4 carbon atoms, and n is 0, 1 or 2.

2. A compound according to claim 1 in which Az denotes an imidazol-1-yl or 1,2,4-triazol-1-yl radical, R denotes a phenyl or benzyl radical which is optionally monosubstituted or disubstituted by chlorine, fluorine or methyl, or denotes a naphthyl, naphthylmethyl, tetrahydronaphthyl, tetrahydronaphthylmethyl radical, $R^1$ denotes a chlorine or fluorine atom or a methyl, ethyl or isopropyl group and n is 0 or 1.

3. The compound of the formula

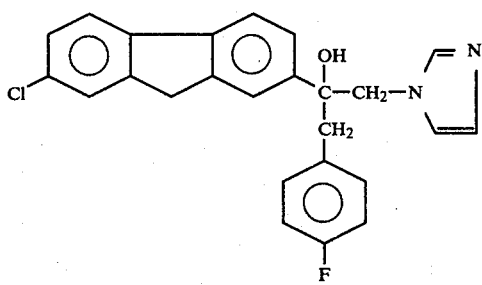

4. The compound of the formula

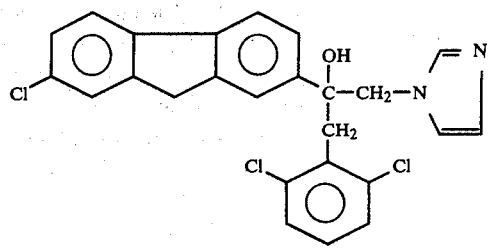

5. The compound of the formula

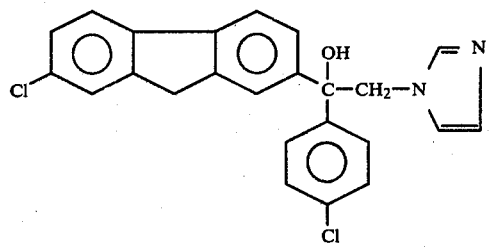

6. The compound of the formula

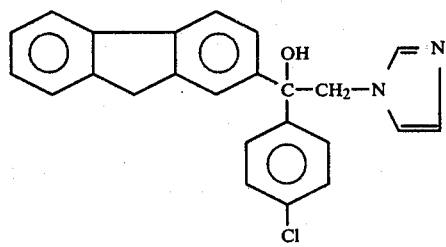

7. A pharmaceutical composition containing as an active ingredient an antimycotically effective amount of a compound according to claim 1 in admixture with a solid, liquid or liquefied gaseous diluent.

8. A pharmaceutical composition according to claim 7 in the form of a sterile or physiologically isotonic aqueous solution.

9. A composition according to claim 7 or 8 containing from 0.5 to 95% by weight of the said active ingredient.

10. A medicament in dosage unit form comprising an antimycotically effective amount of a compound according to claim 1 together with an inert pharmaceutical carrier.

11. A medicament of claim 10 in the form of tablets, pills, dragees, capsules ampoules, or suppositories.

12. A method of combating mycoses in warm-blooded animals which comprises administering to the animals an antimycotically effective amount of an active compound according to claim 1 either alone or in admixture with a diluent or in the form of a medicament.

13. A method according to claim 12 in which the active compound is administered in an amount of 50 to 200 mg per kg body weight per day.

14. A method according to claim 12 or 13 in which the active compound is administered parenterally.

* * * * *

UNITED STATES PATENT AND TRADEMARK OFFICE
CERTIFICATE OF CORRECTION

PATENT NO. : 4,239,765
DATED : December 16, 1980
INVENTOR(S) : Erik Regel, et al.

It is certified that error appears in the above—identified patent and that said Letters Patent is hereby corrected as shown below:

Column 2, line 54 "aton" should be --atom--.
Column 3, line 4 2nd formula at top of page omitted please inert  - CH(N)·

Column 5, line 36 circle omitted from hexagon

Column 6, line 61, "1,34" should be --1,3,4--.
Column 8, line 34 "phospheric" should be --phosphoric--.

Column 9, line 40 "capsuled" should be --capsules--.

Column 10, lines 36-37, "microcrysalline" should be
    --microcrystalline--.

UNITED STATES PATENT AND TRADEMARK OFFICE
CERTIFICATE OF CORRECTION

PATENT NO. : 4,239,765

DATED : December 16, 1980

INVENTOR(S) : Erik Regel, et al.

It is certified that error appears in the above—identified patent and that said Letters Patent is hereby corrected as shown below:

Column 11, line 36 "indivisual" should be --individual--.

Column 13, line 39 "seperated" should be --separated--.

Column 13, line 62 "crystalls" should be --crystals--.

Column 14, line 64 "coverted" should be --converted--.

Signed and Sealed this

Fourteenth Day of April 1981

[SEAL]

Attest:

RENE D. TEGTMEYER

Attesting Officer

Acting Commissioner of Patents and Trademarks